United States Patent [19]

Frazier

[11] 4,253,467
[45] Mar. 3, 1981

[54] ARTHROSCOPIC PROBE

[76] Inventor: Calvin H. Frazier, 1808 Verdugo Blvd., Glendale, Calif. 91208

[21] Appl. No.: 90,675

[22] Filed: Nov. 2, 1979

[51] Int. Cl.³ .............................................. A61B 1/00
[52] U.S. Cl. .................................. 128/630; 128/772; 128/4
[58] Field of Search ........................................ 128/4–9, 128/303, 305, 347, 348, 349, 350, 772, 630

[56] References Cited

U.S. PATENT DOCUMENTS

| | | | |
|---|---|---|---|
| 3,640,281 | 2/1972 | Robertson | 128/349 R X |
| 3,656,485 | 4/1972 | Robertson | 128/349 R |
| 3,656,486 | 4/1972 | Robertson | 128/349 R |

OTHER PUBLICATIONS

Codman–General Surgical Instruments, p. 200.

Primary Examiner—Stephen C. Pellegrino
Attorney, Agent, or Firm—William C. Conkle

[57] ABSTRACT

An apparatus and method for inserting an arthroscope into a knee. A stiff wire probe is shaped to be inserted through an anterior portal of the knee, to pass through the posteromedial cavity, or any other knee cavity, and thence emerge out through the skin. A tapered sleeve having one end configured to connect to the probe and another end configured to receive the arthroscope in a slip fit connects the arthroscope to the probe. Once the arthroscope is received in the sleeve, the arthroscope is pushed into position. Thereafter, the probe and sleeve are withdrawn through the anterior portal.

12 Claims, 4 Drawing Figures

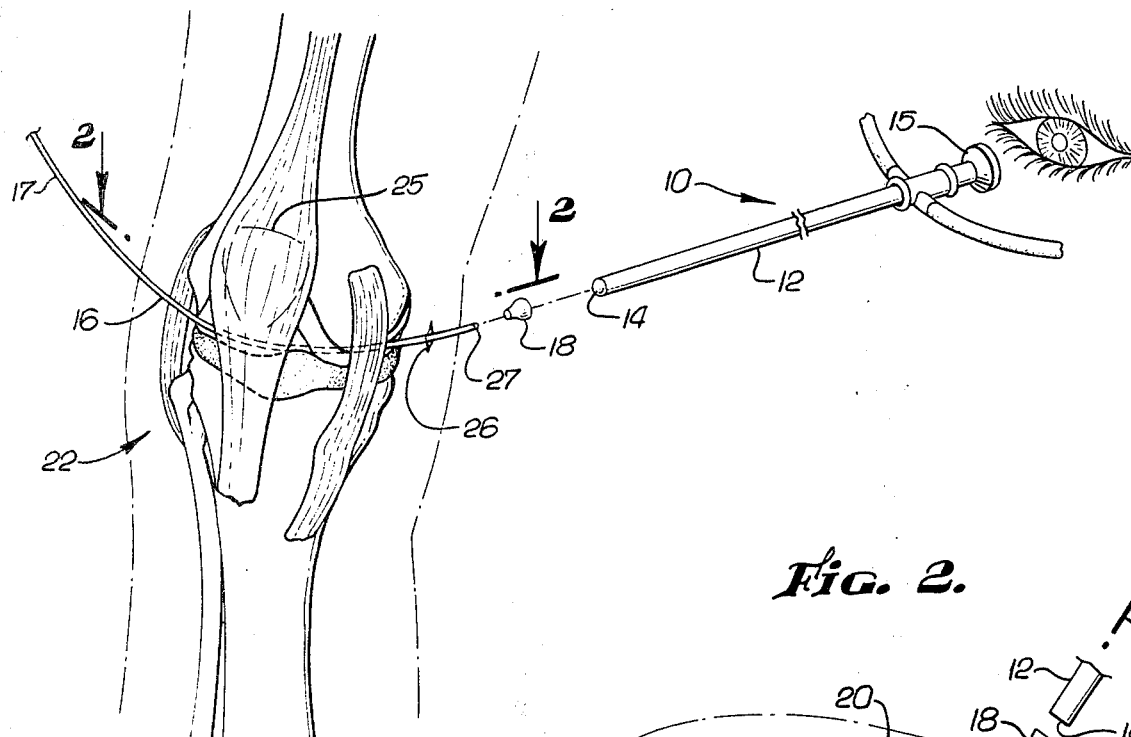
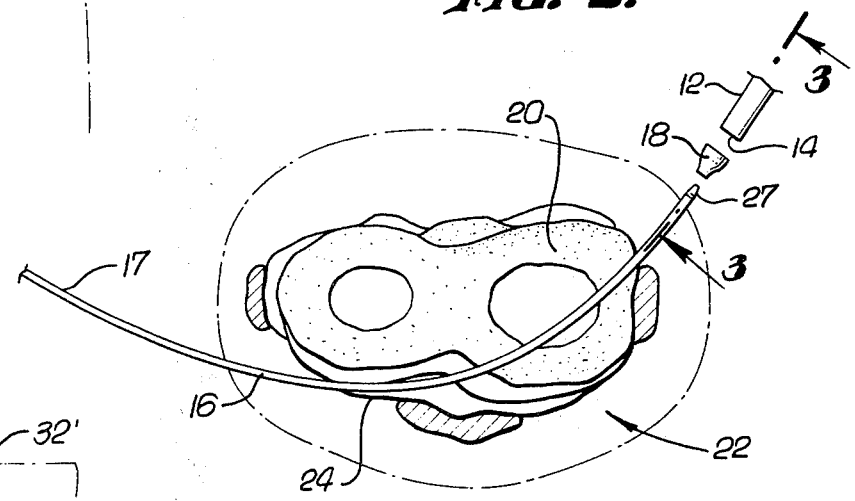
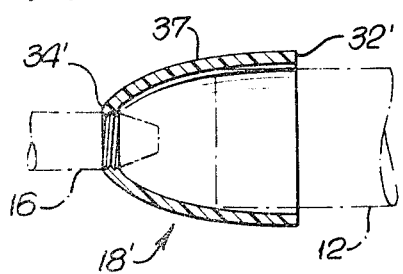
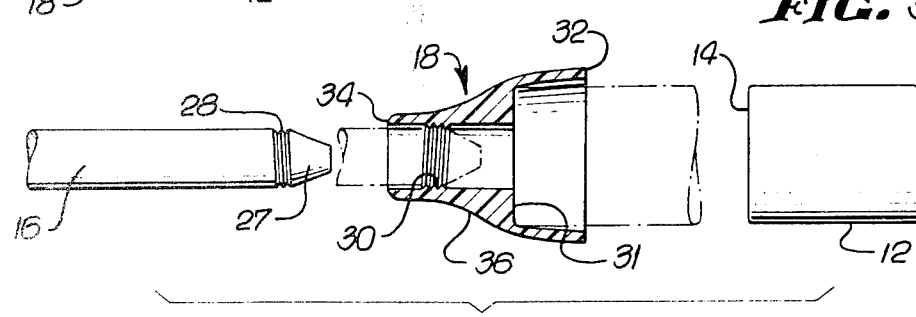

ARTHROSCOPIC PROBE

BACKGROUND OF THE INVENTION

The invention relates generally to surgical instruments and more particularly to an instrument and a method of using the instrument to insert and locate an arthroscope within a human body.

Arthroscopes are devices used to enable the doctor to view the interior of a portion of a body. The arthroscope is a long tube typically made of fiber optics which permits light to be shown down the tube into the body and further permits the doctor to view the body portion adjacent the leading end of the arthroscope. Arthroscopes can be particularly useful in observing the conditions inside a human body. However, because of the shape of their viewing ends, arthroscopes cannot be readily inserted into the restricted areas, or areas crowded with ligaments, tendons and muscle.

One area of the human body in which arthroscope viewing can be extremely useful is in the knee. A surgeon frequently finds it highly desirable to view the posteromedial compartment of the knee to observe conditions in the compartment and to view the cartilage adjacent to the compartment. However, because the knee is crowded with ligaments, tendons and cartilage, it is difficult to insert the arthroscope into the postermedial compartment. Moreover, such insertions into some compartments such as the posteromedial compartment frequently require the relocation or removal by tearing, or cutting, of tissue in the path of the arthroscope.

Hence, there has existed a need for a device which can quickly and accurately locate an arthroscope inside a human knee, and especially inside the posteromedial compartment of the knee. Ideally, such device should permit a surgeon to insert and place the arthroscope precisely the location he wishes it on his first attempt without any unnecessary removal, or destruction, of tissue. The device should permit the location of its leading end or its path to be moved or adjusted by the doctor with only one hand manipulation. Finally, the device should be inexpensive to fabricate and easy to keep sterile.

The present invention fulfills the above described need.

SUMMARY OF THE INVENTION

Briefly and in general terms the present invention provides a new apparatus, and a method for using the apparatus, for surgically inserting an arthroscope into a precisely predetermined location within a human knee.

Basically, a rigid curved probe is inserted through the desired pre-determined location in the center of the knee, from the front of the knee in a direction opposite the direction along which the arthroscope will enter the knee. An end of the probe is allowed to exit the skin adjacent the knee and a sleeve is connected to that end of the probe. The arthroscope is slipped into the sleeve and is then pushed into the knee, the arthroscope being guided in the trace or path of the probe as the probe is withdrawn. When the arthroscope is in position in the knee, the sleeve is pulled free of the arthroscope, and the probe and sleeve are completely withdrawn from the knee along the line of probe insertion.

The probe is small and easy to fabricate. Its threaded portion connects and locks with the sleeve in three revolutions. The probe is curved so that its trace will match the interior geometry of the portion of the joint where it is to be used. By using the probe and sleeve, a surgeon can save approximately 15 minutes in inserting an arthroscope.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 1 is a generally anterior view of a human knee showing a probe inserted through an anterior portion of the knee, a sleeve and an arthroscope;

FIG. 2 is a sectional view of a knee taken in the direction of arrows 2 in FIG. 1 and showing the probe exiting from the posteromedial compartment of the knee;

FIG. 3 is a fragmentary front elevational view, partially in section of the probe, the sleeve and the arthroscope;

FIG. 4 is a view substantially similar to the view in FIG. 3 showing an alternative shape for the sleeve.

DESCRIPTION OF THE PREFERRED EMBODIMENT

As shown in the exemplary drawings, particularly FIGS. 1 and 2, the present invention is embodied in an apparatus used to guide the insertion of an arthroscope 10 into a body. The arthroscope 10 includes a cylindrical tubular wall 12 terminating in a forward blunt viewing end 14. At a location remote from the viewing end 14 and by means of optical apparatus 15 a doctor can view the material in the vicinity of the viewing end of the arthroscope.

In accordance with the present invention, the arthroscope 10 can be accurately positioned in a predetermined location within the knee by inserting a stiff probe 16 through that predetermined location from a direction opposite to the desired path of entry of the arthroscope. A sleeve 18 is attached to the probe 16 and the arthroscope 10 is introduced into the sleeve. The arthroscope 10 is pushed into the knee as the probe 16 is simultaneously retracted. In this way the probe 16 guides the arthroscope 10 into the predetermined location in the knee. By using the apparatus of the invention in the described method, the arthroscope 10 can be accurately placed within a constricted region of the body such as the posteromedial compartment 20 of a knee 22.

More particularly as shown in FIG. 3, the probe 16 is an elongated stiff member having a rounded external surface. The precise shape of the probe's 16 cross section, taken perpendicular to its axis, is not of critical importance, but the probe's surface should be configured so as to permit the probe to pass freely along or between ligaments, tendons, tissue and bone. Probes having circular cross sections will operate satisfactorily.

As is shown in FIG. 2, the probe 16 is curved so that, when it is resting on a flat surface, a portion near its end describes an arc having a radius of about 4 centimeters. This arc shape permits a doctor to control the direction of entry of the probe 16 by rotating the trailing end 17 of the probe as he advances the probe into the body. Moreover, the arc is configured to fit the internal geometry of the knee 22 so that when the probe is inserted through an anterior portal 24 lying near the patella 25, the probe can be advanced along the curved path through the posteromedial compartment 20.

The probe 16 is inserted through the knee 22 until it protrudes under the skin covering the knee. A small incision 26 is made to permit the probe 16 to emerge through the skin. The probe 16 is then joined to the sleeve 18. The arthroscope 10 is slipped into the sleeve 18 and as the probe 16 and sleeve are pulled back through the posteromedial compartment 20, the arthroscope is pushed into the knee 22 thereby keeping the arthroscope in the sleeve and causing the arthroscope to follow the trace of the probe.

A portion of a leading end 27 of the probe 16 has male screw threads 28. These male threads 28 are received by female threads 30 in the sleeve 18, and the threads cooperate to join the probe 16 and the sleeve. The threads are configured so that in three revolutions of the sleeve 18 with respect to the probe 16, the probe and sleeve are locked together. It will be apparent that other methods of attaching the probe 16 and sleeve 18 together, could be successfully used.

The sleeve 18 receives the arthroscope 10 in a loosely fitting slip fit. In the sleeve 18 illustrated in FIG. 3 a step 31 inside the sleeve abuts the blunt end 14 of the arthroscope 10. The step prevents the arthroscope 10 from becoming jammed within the sleeve 18 when the arthroscope is being pushed into the knee. The loose slip fit between the sleeve 18 and the arthroscope 10 permits the sleeve to be disconnected easily once the arthroscope is in place. The doctor merely continues to withdraw the probe 16 and the sleeve will slip off the arthroscope 10 once the doctor stops pushing the arthroscope into position.

As is shown in FIGS. 3 and 4, the ends of the sleeve 18 are sized to be capable of engaging the arthroscope 10 on an end 32 having a large diameter and the probe on an end 34 having a small diameter. The sleeve ends 32 and 34 are connected by a central portion 36 whose walls converge toward each other in a direction toward the small end 34. The convergence or taper of central portion 36 when viewed along a longitudinal cross section can be either a straight line or a line having at least one curve. When such a curved central portion 36 is used, the curved portion preferably joins the ends 32 and 34 at points of tangency.

An alternative embodiment of the sleeve 18' is shown in FIG. 4 and its portions which find substantial correspondence to those previously discussed in connection with FIGS. 1 through 3 are designated with corresponding primed numerals. A central portion 37 of sleeve 18' of the alternative embodiment has a bell shaped taper along its congitudinal cross section.

Regardless of the shape of the tapers, the leading portion of the sleeve 18 adjacent the probe 16 should not have a sharp or blunt edge between the sleeve sidewall 32 and the threaded portion, such a sharp break appearing in its longitudinal cross section which might snag or tear human tissue. Rather the sleeve's 18 leading surface should present a tapered or curved edge such as those illustrated in FIGS. 3 and 4.

When the surgeon has connected the probe 16 to the arthroscope 12 as shown in FIG. 3, he can, by pulling on the probe, and pushing the arthroscope, place the arthroscope 10 into the predetermined position, within the knee 22. After the arthroscope 12 is positioned, the sleeve 18 is withdrawn. The surgeon continues to pull on the probe 16 until both probe and sleeve 18 have been removed from the knee 22. The surgeon can then use the arthroscope 10 in the conventional manner.

From the foregoing description, it will be apparent that the probe 16 and sleeve 18 of the invention permit a doctor to accurately locate the blunt viewing end 14 of a arthroscope 10 within a compartment of the knee 22 without undue damage to ligaments, tendons, tissue or bone. Using the apparatus and method of the invention, the doctor can insert the probe 16 into the knee 22 compartment from a side opposite the desired point of entry of the arthroscope 10, connect the probe to the arthroscope, and draw the arthroscope into position. The arc shape of the probe 16 permits facile manipulation of the probe during insertion and the quick working connection between the probe and sleeve 18 permits the rapid attachment of the arthroscope to the probe.

While a particular form of the invention has been illustrated and described, it will be apparent that various modifications can be made without departing from the spirit and scope of the invention.

I claim:

1. An apparatus for use in a surgical insertion of an arthroscope of the type having a blunt viewing end into a predetermined location within a human knee, said apparatus comprising:
   a rigid probe having a leading end, said probe adapted to be inserted from an anterior portal of said knee through the center of said knee;
   means for temporarily connecting said probe to said arthroscope comprising a sleeve configured at a first end to engage said leading end of said probe and configured at a second end to receive said arthroscope, each of said ends having cylindrical portions of a fixed diameter, the cylindrical portion of the second end having a greater diameter than that of the first end, said sleeve ends being joined by a central portion having a wall that tapers to a smaller diameter in a direction toward the first end.

2. An apparatus as described in claim 1 wherein said probe has a rounded external shape adapted for easy passage within the constricted portions of the human body and has a curved portion describing an arc.

3. An apparatus as described in claim 1 wherein said sleeve is disconnectable from said probe.

4. An apparatus as described in claim 2 wherein:
   said probe has a generally cylindrical axial cross sectional area having a diameter of about two millimeters; and
   said arc shaped portion has a radius of 4 centimeters.

5. An apparatus as described in claim 1 wherein said coupling means comprises male screw threads on said probe and corresponding female screw threads on said sleeve, said threads configured so that three revolutions of said sleeve with respect to said probe lock said probe and sleeve into engagement.

6. An apparatus as described in claims 1 wherein in a longitudinal cross section said walls describe a generally straight line.

7. An apparatus as described in claim 1 wherein in a longitudinal cross section said walls describe a line having at least one curve.

8. An apparatus for use in a surgical insertion of an anthroscope into any compartment of a human knee comprising:
   a probe adapted to be inserted through the knee having a generally cylindrical axial cross section, said portion having a diameter of about 2 millimeters, said probe having a curved portion that describes an arc having a radius of about 4 centimeters, said probe having a leading end including male threads; and a sleeve adapted to receive an anthroscope at a second end and having female threads for engaging said male threads on said probe at a first end, said threads configured so that three revolutions of said sleeve with respect to said probe act to lock said probe and sleeve together, said second of said two cylindrical ends having the greater diameter, said ends being joined by a central portion whose walls in longitudinal cross section taper inwardly in a direction toward said first end.

9. An apparatus as described in claim 8, wherein said walls taper along a line having at least one curve.

10. An apparatus as described in claim 8, wherein said walls taper in a generally straight line.

11. A method for surgically inserting an arthroscope having a blunt end into a predetermined position within a human knee, said method comprising:

inserting a stiff probe through an anterior portal of the knee;

pushing said probe from said portal of the knee through said predetermined position within a center portion of the knee and out through the skin adjacent another portion of the knee;

attaching a first end of a sleeve to said probe;

inserting the arthroscope into a second end of said sleeve;

pushing said arthroscope into said knee in the path of said probe while simultaneous withdrawing said probe and sleeve.

12. The method described in claim 11, further comprising:

holding said arthroscope in said predetermined position when said arthroscope has been advanced to said predetermined position;

withdrawing said probe and sleeve through said portal of the knee and out through skin covering the knee.

* * * * *